US006652684B1

United States Patent
Wong

(10) Patent No.: US 6,652,684 B1
(45) Date of Patent: Nov. 25, 2003

(54) GLUE-ON TISSUE MOUNT

(76) Inventor: Ira G. Wong, 930 Viewridge Dr., San Mateo, CA (US) 94403

( * ) Notice: Subject to any disclaimer, the term of this patent is extended or adjusted under 35 U.S.C. 154(b) by 191 days.

(21) Appl. No.: 09/991,824

(22) Filed: Nov. 5, 2001

(51) Int. Cl.[7] .............................................. B32B 31/00
(52) U.S. Cl. ....................... 156/57; 435/40.52; 359/396
(58) Field of Search ........................... 156/57; 435/40.5, 435/40.51, 40.52; 359/396

(56) References Cited

U.S. PATENT DOCUMENTS

| | | | | |
|---|---|---|---|---|
| 2,783,180 A | * | 2/1957 | Whitehead | 156/57 |
| 3,130,099 A | * | 4/1964 | Homburger | 156/57 |
| 3,498,860 A | * | 3/1970 | Pickett | 156/57 |
| 3,737,335 A | * | 6/1973 | Feinberg | 156/57 |
| 3,770,477 A | * | 11/1973 | Weichselbaum | 359/396 |

* cited by examiner

*Primary Examiner*—Jeff H. Aftergut

(57) ABSTRACT

The glue-on tissue mount is a device to hold small and/or irregular-shaped biologic tissue so tissue can be manipulated, cut, trimmed, split or divide for transplant and reconstructive surgery. Biologic tissue is quickly mounted onto an acrylic mount with fast-bonding cyanoacrylate glue. On the mount tissue can be held firmly. The tissue can be cut on the mount like on a cutting board or dissected into layers. The mount can rest on flat surfaces and be used with an operating microscope or held between fingers. The glue-on tissue mount has a spherical acrylic mounting surface 12 or flat acrylic mounting surface 14 upon which the tissue is glued. The size and shape of the tissue determines if a spherical or flat mount is used. The mounting surface is attached to a cylindrical base 10 that is easily held. If the glue adhesion breaks the tissue can be anchored with sutures tied to the eyelets in the hexagonal footing of the base 10. The glue-on tissue mount can be used for cutting a variety of biologic tissue or biologic material.

4 Claims, 2 Drawing Sheets

GLUE-ON TISSUE MOUNT

FEDERALLY SPONSORED RESEARCH

Not Applicable

SEQUENCE LISTING OR PROGRAM

Not Applicable

BACKGROUND—FIELD OF INVENTION

This invention relates to surgery, specifically a medical device to improve the method of cutting, trimming, splitting or dividing biologic tissue.

BACKGROUND—DISCUSSION OF PRIOR ART

Cutting, trimming, splitting or dividing smaller than thumbnail size pieces of biologic tissue is difficult when detached. A small piece of tissue may be irregularly shaped and difficult to hold. Biologic soft tissue is malleable. Just holding tissue with a pair of forceps may distort or stretch the shape and affect the accuracy and precision of a cut.

In transplant and reconstructive surgery tissue is removed, altered and replaced. When a tissue is removed it may be cut, trimmed, split or divided before it is attached.

For example, in grafting skin, the skin graft is trimmed to fits its future site. Holding and shaping a small piece of skin is awkward. Forceps holding tissue may obstruct or distort the cutting or trimming.

For very small irregular-shaped tissue, a surgeon may resort to placing the tissue on the tip of a finger and with the other hand cut the small piece with microsurgical scissors.

Holding a small piece of tissue under an operating microscope is awkward. A piece of tissue has be kept in focus and within the narrow microscope viewing area while trying to precisely cut the tissue.

In some corneal transplant surgery, only part of a donor cornea is used. A dome-shaped donor corneal tissue is placed directly on the operating table and an assistant holds down the donor tissue with forceps while the surgeon dissects a uniformly thin sheet of corneal tissue. Because of its dome shape, the donor cornea does wobbles as the surgeon cuts.

Sometimes a donor cornea tissue is split along its edge to remove a thin layer to be grafted. To achieve a layer of uniform thickness, the upper layer is retracted and dissected from the lower layer. The bottom layer is held down against the tabletop with two forceps. As the surgeon dissects and pulls against the forceps the tissue distorts and stretches, an undesirable effect.

In the past, corneal transplantation surgery used whole donor eyeball to harvest part or whole of a cornea. A whole eyeball provided a stable platform to remove the needed corneal tissue. Today, because of modern donor corneal preservation technique, cornea is completely removed from the donor's eyeball at the time of harvesting. Days later the cornea tissue is transplanted. Without the support of the rest of the eye, donor cornea tissue is difficult to hold.

A method to hold the cornea is to tie the dome-shaped donor tissue around a ball. A donor cornea is stretched and wrapped around a ball with suture. Another method is to pin down the cornea onto a ball with needles. The needles interfere with the cutting. Both procedures are awkward, time-consuming and potentially damaging to the donor tissue. The ball does not provide a stable base for cutting.

Objects and Advantages

Accordingly, several objects and advantages of my invention are:

a. small and/or irregular-shaped piece of biologic tissue is held firmly by the invention eliminating the need for forceps or other fixating instruments b. attachment of tissue to the device is simple and quick c. biologic tissue is held firmly by the device d. the device can be grasped, tilted or rotated for optimum viewing or manipulating of mounted biologic tissue e. the device provides a solid cutting surface to make accurate and precise cuts f. the device grasp is strong enough to counter the retraction during lamellar dissection g. the device originally designed for corneal surgery can be used for any other surgery, human or veterinary, or in situations where small and/or irregular shaped biological material need to be manipulated, cut, trimmed, dissected or split.

SUMMARY

The invention is a medical device to hold small and/or irregular-shaped t biologic tissue by gluing tissue with quick-bonding cyanoacrylate glue onto an acrylic mount. Once glued on the mount tissue can be cut, trimmed, split or divided more accurately than holding a small piece manually.

DRAWINGS

Drawing Figures

Figure 1:
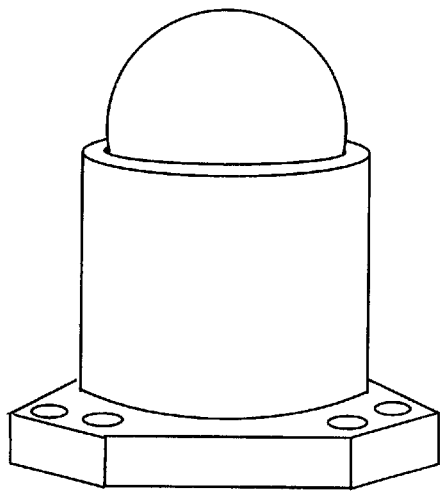
FIG. 1 is a perspective of my invention with spherical mounting surface.

REFERENCE NUMERALS IN DRAWINGS
Part Name
10 Base
12 Mounting surface-acrylic sphere
14 Mounting surface-acrylic disk

DETAILED DESCRIPTION

FIGS. 1, 2, 3, 4

Figure 2:
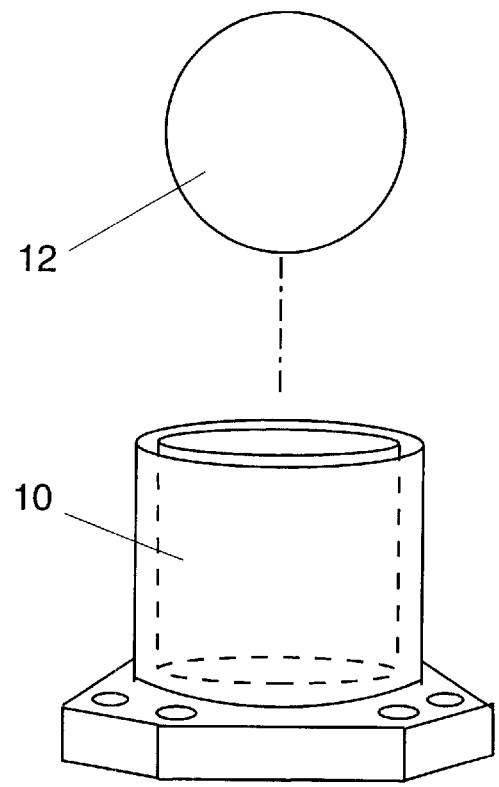
FIG. 2 is an exploded view of the spherical-shaped mount.
Figure 3:
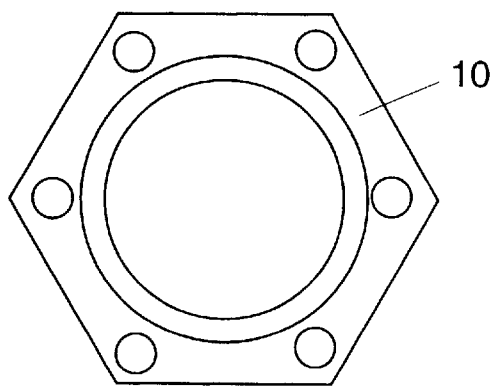
FIG. 3 is a top view of the spherical-shaped mount.
Figure 4:
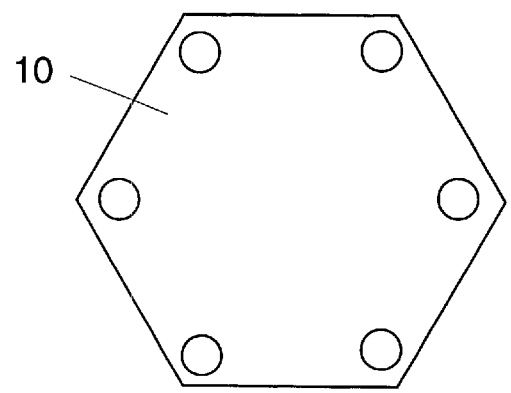
FIG. 4 is the bottom view of the mount.

FIG. 1 shows a perspective view of the mount with a spherical surface and FIG. 2 is an exploded view showing the parts. FIGS. 3 and 4 are top and bottom views.

The spherical mounting surface is an acrylic sphere 12 attached to a base 10.

Biologic tissue is attached to the spherical acrylic surface 12 with cyanoacrylate glue.

The base 10 is a cylindrical tube with a hexagonal-shaped footing. The cylindrical tube is of such height to be easily grasped with fingers. At each hexagonal corner of the footing is an eyelet or hole or large enough to be threaded by needle and suture.

OPERATION OF INVENTION

A small amount of cyanoacrylate glue is applied to the undersurface of the biologic tissue to be cut, trimmed, divided or split. The tissue is than placed onto the acrylic contact surface 12. Light pressure is applied to the tissue to assure good adhesion. After one minute the tissue is bonded to the acrylic sphere (part 12.

The base 10 can be grasped with fingers or stand freely on a flat surface under an operating microscope. The base 10 can be rotated or tilted on one its hexagonal edges to improve visualization of the tissue. The hexagonal-shaped footing of the base 10 prevents rocking when the apparatus is tilted for observation or manipulation.

If the glue adhesion is broken during tissue retraction, additional glue can be applied. Alternatively, a loose edge can be tacked down by tying down the edge to an eyelet in the hexagonal footing of the base 10 with suture.

DESCRIPTION AND OPERATION OF ALTERNATIVE EMBODIMENTS

FIGS. 6, 7, 8

Depending on the size and shape of tissue, gluing a tissue onto a flat surface may be preferred to a spherical surface. For tissue like skin, a flat mounting surface is preferred. For donor cornea tissue a spherical mounting surface is preferred.

Figure 5:
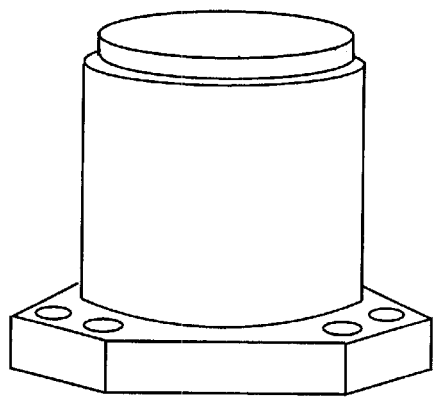
FIG. 5 is a perspective view of a second embodiment of the mount with a flat mounting surface.
Figure 6:
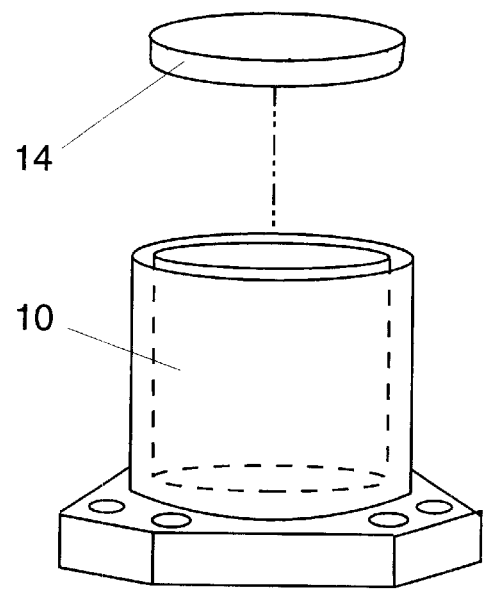
FIG. 6 is an exploded view of the flat-surface mount.
Figure 7:
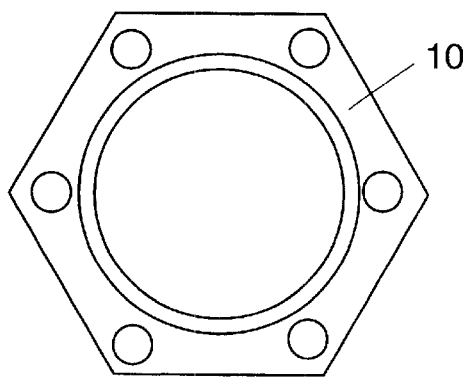
FIG. 7 is a top view of the second embodiment of the mounting block with a flat mounting surface.

FIG. 5 shows the mounting block with a flat cutting surface and FIG. 6 shows an exploded view. The flat cutting surface is an acrylic disk 14 attached to the base 10 as illustrated in FIG. 5. FIG. 7 is a top view. The bottom view is a duplicative view of the first embodiment, FIG. 4.

The operation of the flat surface mount is the same as the spherical mount. A small amount of cyanoacrylate glue is applied to the tissue and the tissue is set onto the flat acrylic surface. A minute later the tissue is ready to be manipulated, cut, trimmed, divided or split.

CONCLUSION, RAMIFICATIONS AND SCOPE OF INVENTION

Thus the reader will see that the glue-on tissue mount provides a simple, quick method to perform precise and accurate cutting, trinmming, dividing and splitting of small, sometimes irregular-shaped biologic tissue that will be transplanted or attached. Gluing the tissue onto acrylic material is a key element in being able to hold and maneuver small and/or irregular-shaped tissue. The mount offers a stable backing to cut, trim, divide or split the tissue. The short bonding time for the cyanoacrylate glue makes attachment quick.

While my above description contains many specificities, these should not be construed as limitations on the scope of the invention, but rather as an exemplification of one preferred embodiment thereof. Many other variations are possible. This application describes spherical and flat mounting surfaces. The acrylic mounting surface can be modified to accommodate other size and shaped biologic material. This application describes the glue-on mounting technique for human or veterinary surgery. In addition, the technique can be used with other biologic material for commercial, manufacturing or research purposes.

Accordingly, the scope of the invention should be determined not by the embodiments illustrated, but by the appended claims and their legal equivalents.

I claim:

1. An apparatus for mounting small and/or irregular shaped biologic tissue, comprising:
   a. an acrylic mounting surface for mounting the tissue;
   b. a cylindrical base attached to and supporting the acrylic mounting sphere to provide a grip to manipulate said apparatus; and;
   c. cyanoacrylate glue as means for attaching biologic tissue to said acrylic mounting surface
   whereby said mounting surface provides a stable base for holding small tissue.

2. The apparatus of claim 1 wherein the acrylic mounting surface is in the form of a sphere.

3. The apparatus of claim 1 wherein the acrylic mounting surface is in the form of a sphere.

4. A method of holding biological tissue comprising the steps of:
   a. providing an acrylic mounting surface for mounting the tissue thereon;
   b. providing a cylindrical base attached to and supporting the acrylic mounting surface to provide a grip to manipulate the mounting surface;
   c. applying quick bonding cyanoacrylate glue to the biological tissue, and;
   d. mounting the tissue onto the acrylic mounting surface for bonding;
   whereby said cyanoacrylate glue and acrylic material are a means for affixing and providing stabilization to the biological tissue.

\* \* \* \* \*